US008858911B2

(12) United States Patent
Li et al.

(10) Patent No.: US 8,858,911 B2
(45) Date of Patent: Oct. 14, 2014

(54) PHOSPHODIESTERASE 1-TARGETING TRACERS AND METHODS

(75) Inventors: Peng Li, New York, NY (US); Lawrence P. Wennogle, New York, NY (US); Jun Zhao, New York, NY (US); Hailin Zheng, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 0 days.

(21) Appl. No.: 13/500,941

(22) PCT Filed: Oct. 7, 2010

(86) PCT No.: PCT/US2010/002707
§ 371 (c)(1),
(2), (4) Date: Apr. 9, 2012

(87) PCT Pub. No.: WO2011/043816
PCT Pub. Date: Apr. 14, 2011

(65) Prior Publication Data
US 2012/0201754 A1      Aug. 9, 2012

Related U.S. Application Data

(60) Provisional application No. 61/249,855, filed on Oct. 8, 2009.

(51) Int. Cl.
*A61K 51/04*     (2006.01)
*A61K 31/565*    (2006.01)

(52) U.S. Cl.
CPC ................... *A61K 51/0459* (2013.01)
USPC ....... 424/1.89; 424/1.65; 424/1.81; 424/1.85; 514/171; 514/257; 514/262.1; 514/267

(58) Field of Classification Search
USPC .................. 424/484, 486, 489; 514/171, 257, 514/262.1, 263.36, 267; 544/247, 251, 262
See application file for complete search history.

(56) References Cited

U.S. PATENT DOCUMENTS

| | | | |
|---|---|---|---|
| 7,964,607 B2 * | 6/2011 | Verhoest et al. | ........... 514/262.1 |
| 2008/0188492 A1 | 8/2008 | Li et al. | |
| 2010/0087450 A1 * | 4/2010 | Mates et al. | ................. 514/257 |
| 2010/0173878 A1 | 7/2010 | Li et al. | |
| 2010/0273753 A1 | 10/2010 | Li et al. | |
| 2010/0273754 A1 | 10/2010 | Li et al. | |
| 2010/0323997 A1 | 12/2010 | Fienberg et al. | |
| 2011/0237561 A1 | 9/2011 | Li et al. | |
| 2011/0245214 A1 | 10/2011 | Li et al. | |
| 2011/0281832 A1 | 11/2011 | Li et al. | |
| 2011/0312978 A1 | 12/2011 | Davis et al. | |
| 2012/0053190 A1 | 3/2012 | Fienberg et al. | |
| 2012/0071450 A1 | 3/2012 | Li et al. | |
| 2012/0094966 A1 | 4/2012 | Li et al. | |
| 2012/0136013 A1 | 5/2012 | Li et al. | |

OTHER PUBLICATIONS

Adam Vas et al., Clinical and non-clinical investigations using postiron emission tomography, near infrared spectroscopy and transcranial Doppler methods on the neuroprotective drug vinpocetine: A summary of evidences, Jounral of the Neurological Sciences 203-204, (2002), 259-262.*
International Search Report for International Application No. PCT/US2010/002707, mailed on Nov. 23, 2010.
Noguchi et al. "A Facile Preparation of 7-(substituted amino)-6H-pyrrolo[3,4-d]-pyrimidine Derivatives." *Bulletin Chem. Soc. of Japan*, 62(9), 3043-5. (1989).
Gulyás, B. et al, "Pet studies on the brain uptake and regional distribution of [$^{11}$C]vinpocetine in human subjects"; *Acta Neurologica Scandinavica*; 2002; 106; pp. 325-332.
Lourenco, Celia M. et al., "Characterization of R-[$^{11}$C]rolipram for PET imaging of phosphodiesterase-4; in vivo binding, metabolism, and dosimetry studies in rats"; *Nuclear Medicine and Biology*; 2001; 28; pp. 347-358.
Vas, A. et al., "Clinical and non-clinical investigations using positron emission tomography, near infrared spectroscopy and transcranial Doppler methods on the neuroprotective drug vinpocetine: A summary of evidences"; *Journal of the Neurological Sciences*; 2002; pp. 259-262.
U.S. Appl. No. 61/235,888, filed Aug. 29, 2009, Li, et al.

* cited by examiner

*Primary Examiner* — Michael G Hartley
*Assistant Examiner* — Jagadishwar Samala
(74) *Attorney, Agent, or Firm* — Hoxie & Associates, LLC

(57) ABSTRACT

Tracers targeting phosphodiesterase 1 for use in gamma radiation detection-based diagnostic techniques, particularly gamma-emitter labeled tracers for SPECT and positron emitter-labeled compositions for PET are disclosed. Radio-labeled multiple novel scaffolds as PDE1 inhibitors such as substituted pyrazolo-pyrimidin-4-one derivatives, biomarkers for phosphodiesterase 1 [PDE1) in vivo, methods for developing novel therapies for PDE1-implicated conditions such as pulmonary arterial hypertension (PAH), Central Nervous System (CNS) and Cardiovascular (CV) disorders, and methods of detection and treatment are also disclosed.

6 Claims, 3 Drawing Sheets

PHOSPHODIESTERASE 1-TARGETING TRACERS AND METHODS

CROSS REFERENCE TO RELATED APPLICATIONS

This application is a continuation PCT/US 2010/002707, filed Oct. 7, 2010, which claims priority to U.S. Provisional Application No. 61/249,855, filed Oct. 8, 2009, contents of which are each incorporated by reference.

FIELD OF THE INVENTION

The present invention relates to tracers for use in diagnostic techniques, particularly gamma-emitter labeled tracers for SPECT and positron emitter-labeled compositions for PET, biomarkers for phosphodiesterase 1(PDE1) in vivo, methods for developing novel therapies for PDE1-associated conditions such as pulmonary arterial hypertension (PAH), and to methods of detection and treatment. The compositions of particular interest are radiolabeled compositions which selectively bind to PDE1, which is associated with conditions of interest in various tissues and organs. For example, PDE1C is enriched in arterial smooth muscle cells, myocardium and atherosclerotic lesions, with increasing evidence of a linkage of PDE1C to smooth muscle proliferation. Positron emitter-labeled compositions targeting PDE1C would enable PET diagnostic imaging of tissue at risk of functional degradation characteristic of PAH and provide a basis for novel therapies for Central Nervous System (CNS) and Cardiovascular (CV) disorders.

BACKGROUND OF THE INVENTION

Gamma radiation-based imaging techniques employ tracer compounds that are introduced into the body to be imaged. The tracer compounds contain a radionuclide which directly or indirectly releases photons whose locations of origin within the body are then calculated from intercept data gathered by gamma radiation detectors. Two commonly employed gamma radiation-based imaging techniques are Positron Emission Tomography (referred to as PET) and Single Photon Emission Computed Tomography (referred to as SPECT). In PET, the radionuclide indirectly releases a pair of oppositely directed photons. The PET radionuclide emits a positron, which upon contact with an electron in its immediate vicinity triggers anti-matter annihilation of both particles which event emits the pair of photons. In SPECT, the radionuclide is a direct gamma emitter. Examples of isotopes useful in gamma radiation-based imaging include Carbon-11 (referred to as $^{11}C$ or C11), Fluorine-18 (referred to as $^{18}F$ or F18), Technetium-99m (referred to as $^{99m}Tc$ or Tc99m), Indium-111 (referred to as $^{111}In$ or In111) and Iodine-123 (referred to as $^{123}I$ or I123).

In addition to the radionuclide, the tracer compound comprises a ligand which provides an affinity of the tracer to a selected target associated with one or more tissues, organs or conditions of interest.

Among the 11 phosphodiesterase (PDE) families, only PDE1 is calcium and calmodulin activated. Under chronic stress conditions of increased intracellular calcium, therefore, this system is most relevant. The chronic increase in intracellular calcium is well established in hypertension. PDE1 is a family of three sub-types PDE1-A, B, and C. PDE1B is primarily located in the brain. PDE1A is expressed in brain and sperm. PDE1C is enriched in arterial smooth muscle cells, myocardium and atherosclerotic lesions as well as other tissues. There is increasing evidence of a linkage of PDE1C and smooth muscle proliferation and in cardiac hypertrophy associated with heart disease. Until recently the state of the art in the PDE1 field had not progressed to produce suitable-selective and potent inhibitors. The inhibitors used in the literature are known to be very unselective. The fact that PDE1 is capable of hydrolysis of both cAMP and cGMP is another positive aspect that would indicate beneficial effects on both smooth muscle cell proliferation and on pulmonary vascular hypertension. PDE1-specific drug candidates have been developed including several series of agents with nanomolar potencies and remarkable specificities.

BRIEF SUMMARY OF THE INVENTION

According to one aspect of the invention radiolabeled inhibitors of phosphodiesterase 1 are provided.

In another aspect, a method is provided in which PDE1 inhibitors are radiolabeled in the last step of synthesis using chemical methods that are appropriate for the radiochemistry laboratory.

A further aspect of the invention provides PET ligands of excellent radiochemical product yield, chemical purity, and specific activity.

An additional aspect provides PET ligands useful as diagnostic tools to facilitate the identification and development of novel clinical agents for PAH disease.

Another aspect provides biomarkers, such as novel PET ligands, that will report on the target occupancy of the inhibitors and that will allow a proper estimation of drug action.

Another aspect of the invention is to provide new agents for diagnosis and therapy of Pulmonary Arterial Hypertension, Central Nervous System (CNS) and Cardiovascular (CV) disorders.

DETAILED DESCRIPTION OF THE INVENTION

Figure 1:
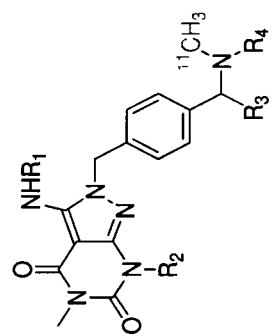
FIG. 1 is an illustration of the preparation of a PET ligand.
Figure 1:
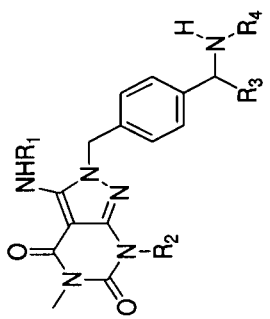
Figure 2:
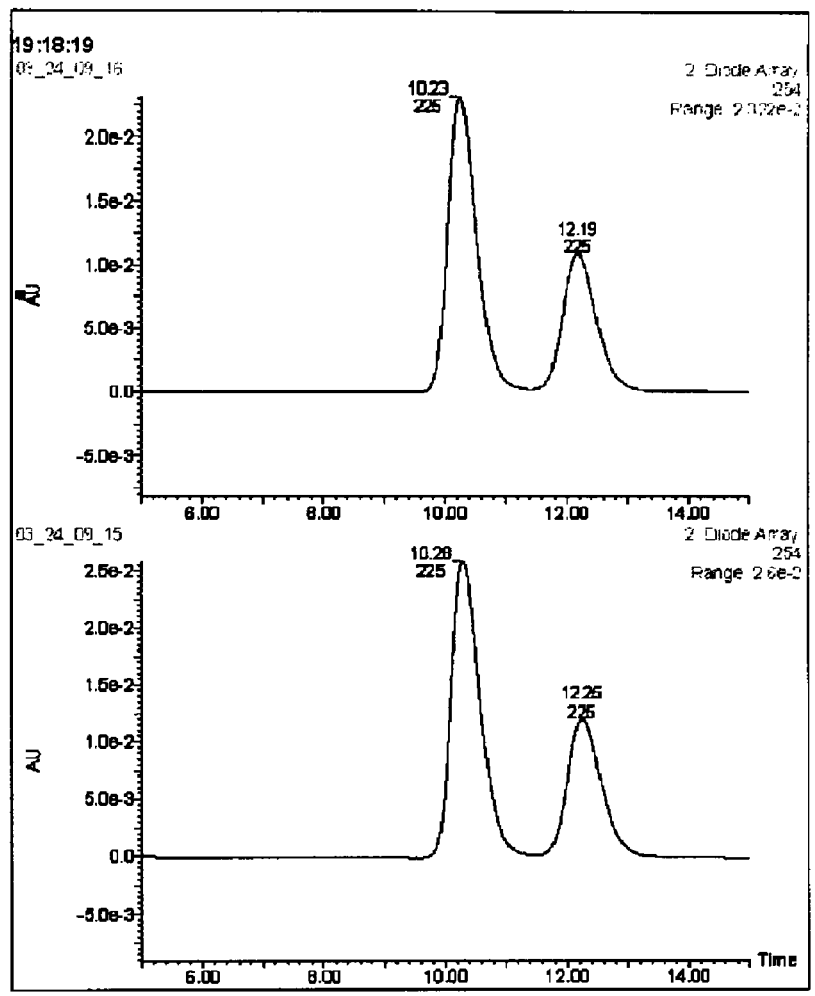
FIG. 2 is an illustration of the results of an HPLC separation.
Figure 3:
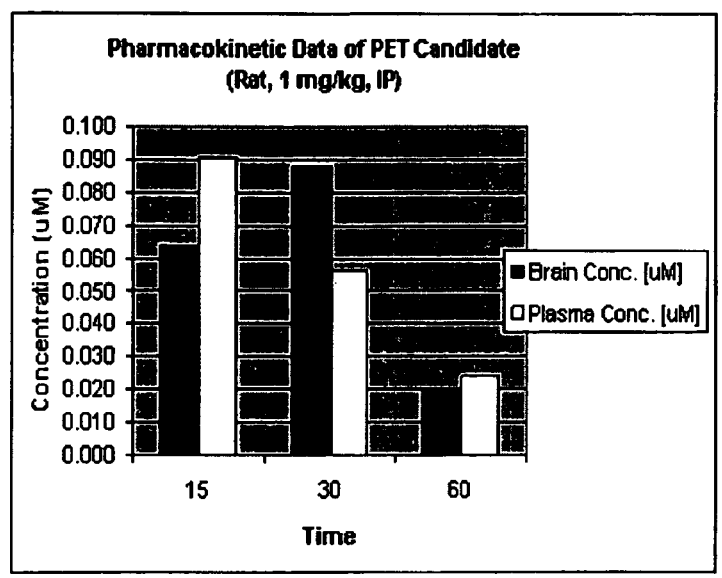
FIG. 3 presents illustrative pharmacokinetics data.

A series of compounds have been discovered to act as inhibitors of phophodiesterase 1 (PDE1), and these PDE1 inhibitors and methods of preparation thereof are thoroughly described in co-pending U.S. patent applications, including Ser. No. 11/916,761 filed on Dec. 6, 2007, published as US-2008-0188492-A1 on Aug. 7, 2008; Ser. No. 12/303,618 filed on Dec. 5, 2008; PCT/US08/13410, filed on Dec. 6, 2008, based upon Provisional Application Ser. No. 61/012, 045 filed on Dec. 6, 2007; PCT/US08/13411, filed on Dec. 6, 2008, based upon U.S. Provisional Application Ser. No. 61/012,040 filed on Dec. 6, 2007; U.S. Provisional Application Ser. No. 61/120,438 filed on Dec. 6, 2008; U.S. Provisional Application Ser. No. 61/120,440 filed on Dec. 6, 2008; U.S. Provisional Application Ser. No. 61/120,441 filed on Dec. 6, 2008; U.S. Provisional Application Ser. No. 61/120, 442 filed on Dec. 6, 2008; U.S. Provisional Application Ser. No. 61/120,443 filed on Dec. 6, 2008; U.S. Provisional Application Ser. No. 61/120,444 filed on Dec. 6, 2008; and U.S. Provisional Application Ser. No. 61/235,888 filed on Aug. 21, 2009, the disclosures of which are hereby incorporated by reference herein as if their contents were set forth at full length herein.

Some particular examples of the classes of compounds which are useful as PDE1 ligands for use in PET or SPECT include radiolabeled derivatives of:

i) 7,8-dihydro-[1H or 2H]-imidazo[1,2-a]pyrazolo[4,3-e]pyrimidin-4(5H)-one;

ii) 7,8,9-trihydro-[1H or 2H]-pyrimido[1,2-a]pyrazolo[4,3-e]pyrimidin-4(5H)-one;

iii) 3-(optionally hetero)arylamino-[2H]-pyrazolo[3,4-d]pyrimidine-4,6(5H,7H)-dione; and iv) (6aR*,9aS*)-3-(phenylamino)-5-6a,7,8,9,9a-hexahydro-5-methylcyclopent[4,5]imidazo[1,2-a]pyrazolo[4,3-e]pyrimidin-4(1H or 2H)-one;

wherein each of (i), (ii), (iii) and (iv) are substituted at the 1- or 2-position with $C_{2-9}$ alkyl, $C_{3-9}$ cycloalkyl, heteroarylalkyl, or substituted arylalkyl.

These PDE1 inhibitors can be modified by replacing an atom in the structure with a radionuclide while maintaining affinity and selectivity of the molecule for PDE1.

The agents are evaluated for inhibition of PDE1 in high-throughput PDE1 enzyme assays and further evaluated against the 11 families of PDE enzymes to identify low nanomolar potency versus PDE1 and greater than 10-fold selectivity to other PDE enzyme families.

Molecular modeling based upon the crystal structures of the PDE1B enzyme as well as the extensive structure-activity relationships built over the past 7 years at ITI has led to a range of compounds with differing pharmacokinetic properties, from those with good brain penetration and long half-lives to those agents unable to enter the brain. We will apply this understanding to measure and optimize PET ligands for use in pulmonary, cardiac and brain tissues.

Another aspect is methods of producing particular selective and potent PDE1 inhibitors, including radiolabeling, for example in the last step of synthesis, using chemical methods that are appropriate for the PET radiochemistry laboratory. Examples of useful radionuclides are Carbon-11 (referred to as $^{11}C$ or C11), Fluorine-18 (referred to as $^{18}F$ or F18), Technetium-99m (referred to as $^{99m}Tc$ or Tc99m), Indium-111 (referred to as $^{111}In$ or In111) and Iodine-123 (referred to as $^{123}I$ or I123). An example of the process is illustrated by Figure I.

Figure 1

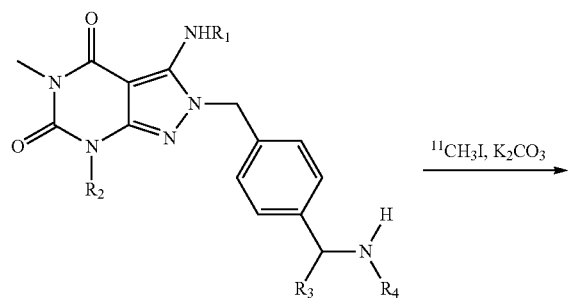

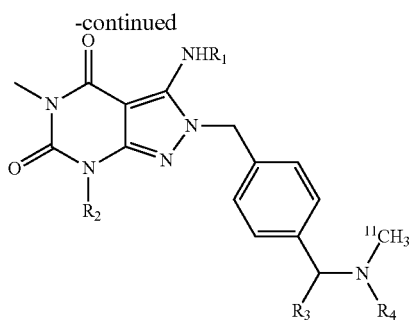

The agents are evaluated for inhibition of PDE1 in high-throughput PDE1 enzyme assays and further evaluated against the 11 families of PDE enzymes to identify low nanomolar potency versus PDE1 and greater than 10-fold selectivity to other PDE enzyme families.

Another aspect is methods of producing multiple series of selective and potent PDE1 inhibitors, including radiolabeling in the last step of synthesis—using chemical methods that are appropriate for the PET radiochemistry laboratory.

A rapid semi-preparative HPLC separation of precursor and product to support the PET radiolabeling is also provided. Such a rapid separation is ideal for a short-lived radioligand such as 11C.

The method implied under this application involves dosing suitable animal species such as rat and baboon and measurement of whole body distribution.

Likewise, the method will entail performing preliminary occupancy studies with unlabeled PDE1 inhibitors.

After labeling, animal or human subjects are dosed with the agent and distribution evaluated over time in appropriate organs. Signal to noise ratio is established and the distribution corresponds to the known distribution of PDE1 in the pulmonary vasculature.

Occupancy studies to evaluate clinical candidates for the ability to occupy PDE1 in these tissues and therefore to block the specific signal of the PET candidate radioligand.

General Baboon PET Methods.

A radial arterial line is placed for radioactive plasma sampling and HPLC metabolism studies. The scanning imaging protocol consists of multiple scans acquisitions over a time period. After acquiring the images the total plasma concentration is determined.

Displacement of Radiotracers by Cold Inhibitors.

Radiotracers meeting the radiochemistry criteria are evaluated for displacement in the lung by cold specific and potent PDE1 inhibitors. The candidate radiotracers are rank ordered with respect to brain uptake, kinetics, displacement by specific cold inhibitors and a lack of displacement by a non-specific cold inhibitor.

Such a ligand will be beneficial in furthering development of novel therapeutic agents and by offering novel PET ligands.

Another aspect is a method to evaluate the effect of pharmacological doses of a related PDE1 inhibitor for effect on sheep and rat models of pulmonary arterial hypertension (PAH).

EXAMPLES

Example 1

Preparation of $^{11}$C-labeled PET ligand, 7-Isobutyl-5-methyl-2-(4-(1-[$^{11}$C]methylpiperidin-2-yl)benzyl)-3-(phenylamino)-2H-pyrazolo[3,4-d]pyrimidine-4,6(5H,7H)-dione (a) (4-(Piperidin-2-yl)phenyl)methanol. To a suspension of LiAlH$_4$ (72 mg, 1.8 mmol) in 2 ml of anhydrous THF is added a solution of methyl 4-(piperidin-2-yl)benzoate hydrochloride (250 mg, 0.98 mmol) in THF dropwise at 0° C. The reaction mixture is stirred at room temperature for 4 hours, and then carefully quenched with water at 0° C. After filtration, the filtrate is evaporated to dryness to give 187 mg of crude product as white solids, which is used for the next reaction without further purification.

(b) Tert-butyl 2-(4-(hydroxymethyl)phenyl)piperidine-1-carboxylate. Crude (4-(piperidin-2-yl)phenyl)methanol (187 mg) is dissolved in 3 mL of DMF, and then Boc anhydride is added. The mixture is stirred at room temperature for 3 hours, and then purified by basic alumina column chromatography to give 200 mg of product as clear oil with a 70% overall yield.

(c) 6-Chloro-1-isobutyl-3-methylpyrimidine-2,4(1H,3H)-dione. A mixture of 6-chloro-3-methylpyrimidine-2,4(1H,3H)-dione (3 g, 18.8 mmol), isobutyl iodide (5 mL, 43.5 mmol) and potassium carbonate (5.3 g, 38.4 mmol) in anhydrous DMF (200 mL) is heated at 50° C. for 8 hours. Additional isobutyl iodide (4.3 mL, 37.5 mmol) is added and the reaction mixture is heated at 50° C. for 24 hours. After hot filtration, the filtrate is evaporated to dryness under reduced pressure. The obtained oil is further purified by silica-gel flash chromatography to give 2.1 g of pure product (Yield: 52%).

(d) 6-Hydrazinyl-1-isobutyl-3-methylpyrimidine-2,4(1H,3H)-dione. To a solution of 6-chloro-1-isobutyl-3-methylpyrimidine-2,4(1H,3H)-dione (2.0 g, 9.3 mmol) in EtOH (8 mL), hydrazine monohydrate (1.3 mL) in EtOH (3 mL) is added slowly. The reaction mixture is refluxed for 5 hours, and then cooled to room temperature. A large amount of ethyl acetate is added into the reaction mixture to precipitate out product. Solid is collected and washed with ethyl acetate to give 1.95 g of product as yellowish solid (Yield: 100%).

(e) 7-Isobutyl-5-methyl-3-(phenylamino)-2H-pyrazolo[3,4-d]pyrimidine-4,6(5H,7H)-dione. Phenyl isothiocyanate (0.17 mL, 1.4 mmol) is added to a solution of 6-hydrazinyl-1-isobutyl-3-methylpyrimidine-2,4(1H,3H)-dione (31 mg, 0.47 mmol) in DMF (10 mL). The reaction mixture is heated at 120° C. for 6 hours, and then evaporated to remove solvent under reduced pressure. The residue is purified by silica-gel flash chromatography to give 20 mg of product (Yield: 41%). $^1$H NMR (400 MHz, DMSO-d6) δ 0.95 (s, 3H), 0.97 (s, 3H), 2.30 (m, 1H), 3.37 (s, 3H), 3.77 (d, 2H), 7.16-7.43 (m, 5H), 7.61 (s, 1H). MS (FAB) m/z 314.3 [M+H]$^+$.

(f) Tert-butyl 2-(4-((7-isobutyl-5-methyl-4,6-dioxo-3-(phenylamino)4,5,6,7-tetrahydropyrazolo[3,4-d]pyrimidin-2-yl)methyl)phenyl)piperidine-1-carboxylate. Tert-butyl 2-(4-(hydroxymethyl)phenyl)piperidine-1-carboxylate (47 mg, 0.16 mmol) is dissolved in 1 mL of anhydrous THF, and then triphenylphosphine (42 mg, 0.16 mmol) is added, followed by 7-isobutyl-5-methyl-3-(phenylamino)-2H-pyrazolo[3,4-d]pyrimidine-4,6(5H,7H)-dione (50 mg, 0.16 mmol). The mixture is cooled to −78° C., and then DIAD (95%, 50 μL) is added slowly. After the reaction is complete, the mixture is purified on a basic alumina column to give 76 mg of product (yield: 81%). MS (ESI) m/z 587.3 [M+H]$^+$.

(g) 7-Isobutyl-5-methyl-3-(phenylamino)-2-(4-(piperidin-2-yl)benzyl)-2H-pyrazolo[3,4-d]pyrimidine-4,6(5H,7H)-dione. Tert-butyl 2-(4-((7-isobutyl-5-methyl-4,6-dioxo-3-(phenylamino)-4,5,6,7-tetrahydropyrazolo[3,4-d]pyrimidin-2-yl)methyl)phenyl)piperidine-1-carboxylate (76 mg) is dissolved in 2 mL of dichloromethane, and then TFA (2 mL) is added. The mixture is stirred at room temperature for an hour. After evaporation, the residue is purified by a semi-preparative HPLC to give 32 mg of pure product as white solids.

(h1) 7-Isobutyl-5-methyl-2-(4-(1-[$^{11}$C)methylpiperidin-2-yl)benzyl)-3-(phenylamino)-2H-pyrazolo[3,4-d]pyrimidine-4,6(5H,7H)-dione. 7-Isobutyl-5-methyl-3-(phenylamino)-2-(4-(piperidin-2-yl)benzyl)-2H-pyrazolo[3,4-d]pyrimidine-4,6(5H,7H)-dione (8 mg, 0.015 mmol) is reacted with [$^{11}$C] methyl iodide in the presence of K$_2$CO$_3$.

Example 2

Preparation of $^{18}$F-labeled PET ligand, 7-lsobutyl-5-methyl-2-(4-(1-[$^{18}$F]fluoromethylpiperidin-2-yl)benzyl)-3-(phenylamino)-2H-pyrazolo[3,4-d]pyrimidine-4,6(5H,7H)-dione The synthetic procedure is similar to that of Example 1, except that in place of the final step (h1), the following step (h2) is followed.

(h2) 7-lsobutyl-5-methyl-3-(phenylamino)-2-(4-(piperidin-2-yl)benzyl)-2H-pyrazolo[3,4-d]pyrimidine-4,6(5H,7H)-dione (8 mg, 0.015 mmol) is reacted with [$^{18}$F]fluoromethyl iodide, [$^{18}$F]fluoromethyl bromide, or [$^{18}$F]fluoromethyl triflate in the presence of a base such as K$_2$CO$_3$ and Cs$_2$CO$_3$, followed by HPLC purification.

Comparative Example 3

Preparation of cold reference, 7-Isobutyl-5-methyl-2-(4-(1-methylpiperidin-2-yl)benzyl)-3-(phenylamino)-2H-pyrazolo[3,4-d]pyrimidine-4,6(5H,7H)-dione The procedure of Example 1 is repeated, except that in place of the final step (h1), the following step (h3) is followed.

(h3) 7-lsobutyl-5-methyl-2-(4-(1-methylpiperidin-2-yl)benzyl)-3-(phenylamino)-2H-pyrazolo[3,4-d]pyrimidine-4,6(5H,7H)-dione. 7-Isobutyl-5-methyl-3-(phenylamino)-2-(4-(piperidin-2-yl)benzyl)-2H-pyrazolo[3,4-d]pyrimidine-4,6(5H,7H)-dione (8 mg, 0.015 mmol) is dissolved in 0.5 mL of anhydrous methylene chloride, and then 37% formaldehyde aqueous solution (5 μL) is added, followed by 20 mg of anhydrous sodium sulfate. After the mixture is stirred at room temperature for 30 min, NaBH$_3$CN (1.4 mg, 0.022 mmol) is added. The reaction mixture is stirred at r.t. for 2 hours, and then purified using a semi-preparative HPLC to give 4.5 mg of product (yield: 55%).

Example 4

Preparation of $^{18}$F-labeled PET ligand, 7-lsobutyl-5-methyl-2-(4-(1-[$^{18}$F]fluoromethylpyrrolidin-2-yl)benzyl)-3-(phenylamino)-2H-pyrazolo[3,4-d]pyrimidine-4,6(5H,7H)-dione (a) Tert-butyl 2-(4-(methoxycarbonyl)phenyl)pyrrolidine-1-carboxylate. 4-(1-(Tert-butoxycarbonyl)pyrrolidin-2-yl)benzoic acid (350 mg, 1.2 mmol) is dissolved in anhydrous methanol (2 mL), and then EDC (310 mg, 1.67 mmol) is added, followed by DIEA (0.3 mL, 1.7 mmol). The mixture is stirred at r.t. overnight, and then diluted with ethyl acetate, washed with saturated sodium bicarbonate aqueous solution and brine successively. Organic phase is evaporated to dryness and purified by silica gel column to give 247 mg of product as an clear oil (yield: 67%).

(b) Tert-butyl 2-(4-(hydroxymethyl)phenyl)pyrrolidine-1-carboxylate. LiAlH$_4$ is suspended in 2 mL of anhydrous THF at 0° C., and then tert-butyl 2-(4-(methoxycarbonyl)phenyl)pyrrolidine-1-carboxylate (238 mg, 0.78 mmol) in anhydrous THF (5 mL) is added dropwise over 5 min. The mixture is stirred at 0° C. for 1 h, and then carefully quenched with 1 mL of water. The mixture is diluted with THF and filtered through a layer of celite. The collected filtrate is evaporated to dryness to give 232 mg of product, which is used for the next reaction without further purification.

(c) Tert-butyl 2-(4-((7-isobutyl-5-methyl-4,6-dioxo-3-(phenylamino)-4,5,6,7-tetrahydropyrazolo[3,4-d]pyrimidin-2-yl)methyl)phenyl)pyrrolidine-1-carboxylate. Tert-butyl 2-(4-(hydroxymethyl)phenyl)pyrrolidine-1-carboxylate (232 mg, 0.84 mmol) is dissolved in 7 mL of anhydrous THF, and then triphenylphosphine (230 mg, 0.87 mmol) is added, followed by 7-isobutyl-5-methyl-3-(phenylamino)-2H-pyrazolo[3,4-d]pyrimidine-4,6(5H,7H)-dione (262 mg, 0.84 mmol). The mixture is cooled to −78° C., and then DIAD (95%, 262 µL) is added slowly. After the reaction is complete, the mixture is purified on a silica gel column to give 227 mg of product as white solid.

(d) 7-Isobutyl-5-methyl-3-(phenylamino)-2-(4-(pyrrolidin-2-yl)benzyl)-2H-pyrazolo[3,4-d]pyrimidine-4,6(5H,7H)-dione. Tert-butyl 2-(4-((7-isobutyl-5-methyl-4,6-dioxo-3-(phenylamino)-4,5,6,7-tetrahydropyrazolo[3,4-d]pyrimidin-2-yl)methyl)phenyl)pyrrolidine-1-carboxylate (227 mg, 0.40 mmol) is dissolved in 3 mL of dichloromethane, and then TFA (1 mL) is added. The mixture is stirred at room temperature for 30 min. After evaporation, the residue is further dried under high vacuum overnight to give 390 mg of product as TFA salts. The crude product is further purified with a semi-preparative HPLC to give pure product.

(e1) 7-Isobutyl-5-methyl-2-(4-(1-[$^{18}$F]fluoromethylpyrrolidin-2-yl)benzyl)-3-(phenylamino)-2H-pyrazolo[3,4-d]pyrimidine-4,6(5H,7H)-dione. 7-Isobutyl-5-methyl-3-(phenylamino)-2-(4-(pyrrolidin-2-yl)benzyl)-2H-pyrazolo[3,4-d]pyrimidine-4,6(5H,7H)-dione is reacted with [$^{18}$F]fluoromethyl iodide, [$^{18}$F]fluoromethyl bromide, or [$^{18}$F]fluoromethyl triflate in the presence of a base such as K$_2$CO$_3$ and Cs$_2$CO$_3$, followed by HPLC purification.

Example 5

Preparation of $^{11}$C-labeled PET ligand, 7-Isobutyl-5-methyl-2-(4-(1-[$^{11}$C]methylpyrrolidin-2-yl)benzyl)-3-(phenylamino)-2H-pyrazolo[3,4-d]pyrimidine-4,6(5H,7H)-dione The procedure of Example 4 is repeated, except that in place of the final step (e1), the following step (e2) is followed.

(e2) 7-Isobutyl-5-methyl-3-(phenylamino)-2-(4-(pyrrolidin-2-yl)benzyl)-2H-pyrazolo[3,4-d]pyrimidine-4,6(5H,7H)-dione is reacted with [$^{11}$C]methyl iodide in the presence of K$_2$CO$_3$.

Comparative Example 6

Preparation of cold reference, 7-Isobutyl-5-methyl-2-(4-(1-methylpyrrolidin-2-yl)benzyl)-3-(phenylamino)-2H-pyrazolo[3,4-d]pyrimidine-4,6(5H,7H)-dione The procedure of Example 4 is repeated, except that in place of the final step (e1), the following step (e3) is followed.

(e3) 7-Isobutyl-5-methyl-2-(4-(1-methylpyrrolidin-2-yl)benzyl)-3-(phenylamino)-2H-pyrazolo[3,4-d]pyrimidine-4,6(5H,7H)-dione. 7-lsobutyl-5-methyl-3-(phenylamino)-2-(4-(pyrrolidin-2-yl)benzyl)-2H-pyrazolo[3,4-d]pyrimidine-4,6(5H,7H)-dione TFA salts (390 mg) is dissolved in 7.5 mL of anhydrous methylene chloride and 2.5 mL of methanol, and then 37% formaldehyde aqueous solution (300 µL) is added. After the mixture is stirred at room temperature for 20 min, NaBH$_3$CN (120 mg) is added. The reaction mixture is stirred at r.t. for 90 min, and then quenched with saturated ammonium chloride aqueous solution. After routine workup, the obtained crude product is purified by silica gel column chromatography to give 112 mg of pure product as white solid.

A series of radiolabeled PDE1 ligand preparations are presented below:

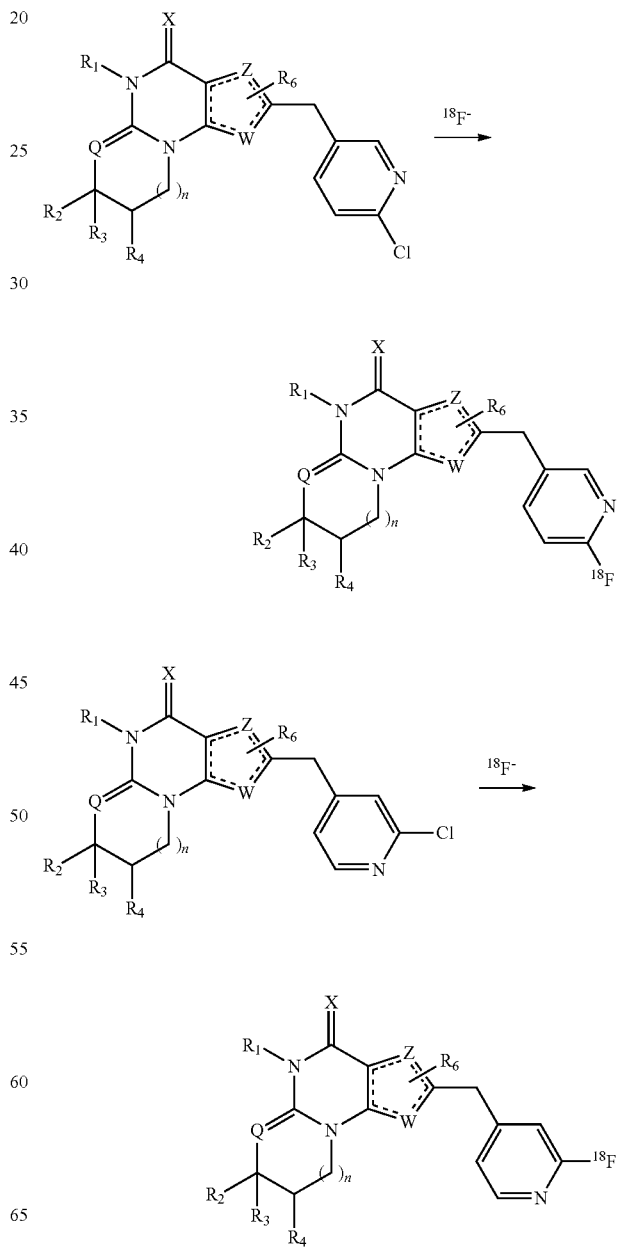

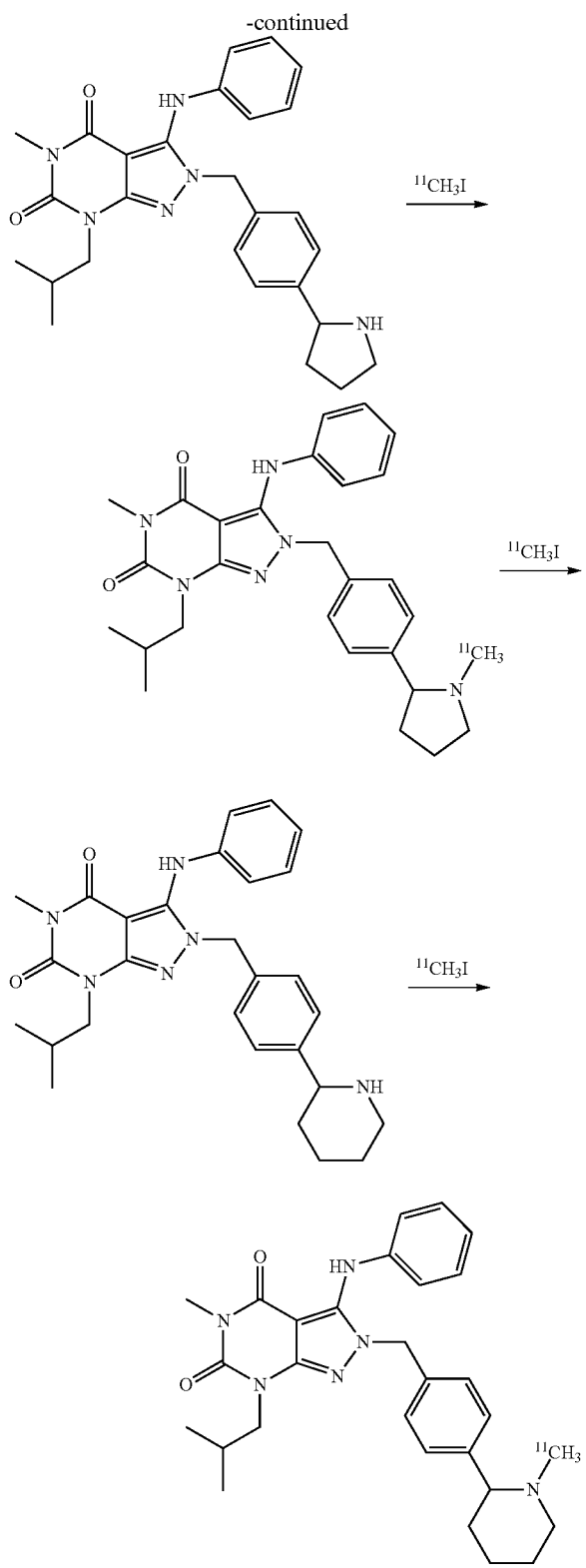

Isolation of the active $^{11}$C-radioligand by HPLC. We have also developed a rapid semi-preparative HPLC separation of precursor and product to support the PET radiolabeling The rapid separation is ideal for a short-lived radioligand such as $^{11}$C. An illustrative printout of an HPLC separation is presented below. In the following diagram, the radiolabeled drug illustrated directly above corresponds to the first peak and is well separated from the precursor peak.

We claim:

1. A radiolabeled phosphodiesterase 1 (PDE1) inhibitor for use in gamma radiation-based diagnostic imaging, wherein the PDE1 inhibitor has low nanomolar potency versus PDE1 and greater than 10-fold selectivity to PDE1 as compared to other PDE enzyme families, and wherein the PDE1 inhibitor is in free or salt form and contains chemically bound radionuclide, and wherein the PDE1 inhibitor is selected from:
   i) 7,8-dihydro-[1H or 2H]-imidazo[1,2-a]pyrazolo[4,3-e]pyrimidin-4(5H)-one;
   ii) 7,8,9-trihydro-[1H or 2H]-pyrimido[1,2-a]pyrazolo[4,3-e]pyrimidin-4(5H)-one;
   iii) 3-(optionally hetero)arylamino-[2H]-pyrazolo[3,4-d]pyrimidine-4,6(5H, 7H)-dione; and
   iv) (6aR*,9aS*)-3-(phenylamino)-5-6a,7,8,9,9a-hexahydro-5-methylcyclopent-[4,5]imidazo[1,2-a]pyrazolo[4,3-e]pyrimidin-4(1H or 2H)-one;
wherein each of (i), (ii), (iii) and (iv) are substituted at the 1- or 2-position with C2-9 alkyl, C3-9 cycloalkyl, heteroarylalkyl, or substituted arylalkyl.

2. The inhibitor of claim 1, wherein the radionuclide is selected from Carbon-11, Fluorine-18, Technetium-99m, Indium-Ill and Iodine-123.

3. A method of selective reversible binding and mapping of functional phosphodiesterase 1 activity in vivo in tissue and/or organ of interest using positron emission tomography which comprises:
   (a) administering an effective amount of a compound of claim 1 to the subject, and then
   (b) allowing a period of time sufficient for the radiotracer to effectively associate with phosphodiesterase1 in the tissues and organs of interest, and then
   (c) analyzing the tissues and organs of interest using positron emission tomography.

4. A therapeutic treatment for phosphodiesterase 1-associated conditions comprising:
   administering the radiotracer inhibitor of claim 1 to a subject, then imaging the subject with a positron emission tomography device, then administering a phosphodiesterase1 inhibitor which does not contain a radionuclide to the subject at a given dose, then imaging the subject with a positron emission tomography device, then comparing the data thus obtained, and assessing the effective delivery of the phosphodiesterase 1 inhibitor to tissue(s) of interest in the phosphodiesterase 1-associated condition.

5. The method of claim 4 wherein the condition is selected from the group consisting of Pulmonary Arterial Hypertension, Central Nervous System Disorders and Cardiovascular Disorders.

6. A radiolabeled phosphodiesterase 1 (PDE1) inhibitor for use in gamma radiation-based diagnostic imaging, wherein the PDE1 inhibitor has low nanomolar potency versus PDE1 and greater than 10-fold selectivity to PDE1 as compared to other PDE enzyme families, and wherein the PDE1 inhibitor is in free or salt form and contains chemically bound radionuclide, and wherein the PDE1 inhibitor is selected from:
   i.) 7-Isobutyl-5-methyl-2-(4-(1-[$^{11}$C]methylpiperidin-2-yl)benzyl)-3-(phenylamino)-2H-pyrazolo[3,4-d]pyrimidine-4,6(5H,7H)-dione;
   ii.) 7-Isobutyl-5-methyl-2-(4-(1-[$^{18}$F]fluoromethylpiperidin-2-yl)benzyl)-3-(phenylamino)-2H-pyrazolo[3,4-d]pyrimidine-4,6(5H,7H)-dione;

iii.) 7-Isobutyl-5-methyl-2-(4-(1-[$^{18}$F]fluoromethylpyrrolidin-2-yl)benzyl)-3-(phenylamino)-2H-pyrazolo[3,4-d]pyrimidine-4,6(5H,7H)-dione; and
iv.) 7-Isobutyl-5-methyl-2-(4-(1-[$^{11}$C]methylpyrrolidin-2-yl)benzyl)-3-(phenylamino)-2H-pyrazolo[3,4-d]pyrimidine-4,6(5H,7H)-dione wherein each of i.)-iv.) is in free or salt form.

* * * * *